United States Patent [19]

Nash

[11] 4,058,898
[45] Nov. 22, 1977

[54] DENTAL BURR

[75] Inventor: John E. Nash, Downington, Pa.

[73] Assignee: Star Dental Manufacturing Co., Inc., Conshohocken, Pa.

[21] Appl. No.: 668,334

[22] Filed: Mar. 19, 1976

[51] Int. Cl.² .............................................. A61C 3/06
[52] U.S. Cl. ...................................................... 32/59
[58] Field of Search ........................ 32/46, 48, 58, 59; 51/206 P, 206 R

[56] References Cited

U.S. PATENT DOCUMENTS

| 278,608 | 5/1883 | Schrebler | 51/206 P |
| 2,697,878 | 12/1954 | Oberley | 32/59 |
| 3,309,772 | 3/1967 | Lieb | 32/48 |
| 3,510,990 | 5/1970 | Steindler | 51/206 R |
| 3,894,339 | 7/1975 | Manzi | 32/59 |

Primary Examiner—Louis G. Mancene
Assistant Examiner—Mickey Yu
Attorney, Agent, or Firm—Joseph I. Hirsch; William B. Walker

[57] ABSTRACT

This application describes a dental burr including a cutting surface having one or more grooves therein, each of the grooves being defined by a plane which encircles the cutting surface at a skewed angle with respect to the axis of rotation of the burr. Such groove(s) provide an oscillatory chip clearing action as the burr rotates to give edge cutting and fast chip clearance. The cutting surface has abrasive particles coated thereon.

7 Claims, 8 Drawing Figures

U.S. Patent    Nov. 22, 1977    4,058,898
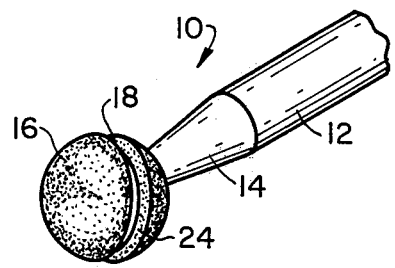
FIG_1
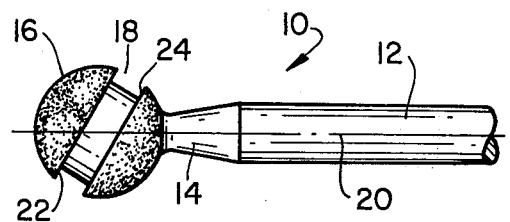
FIG_2
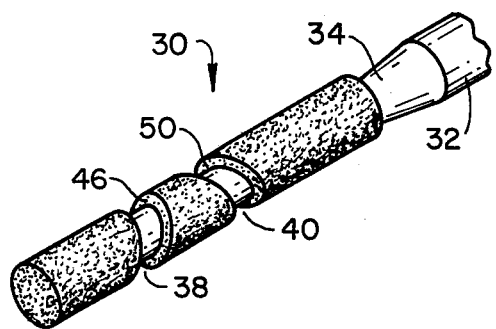
FIG_3
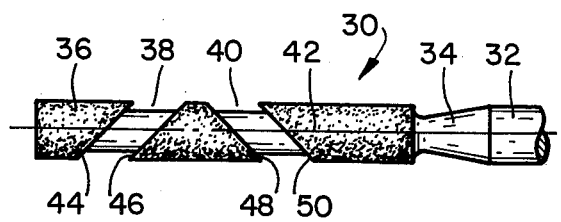
FIG_4
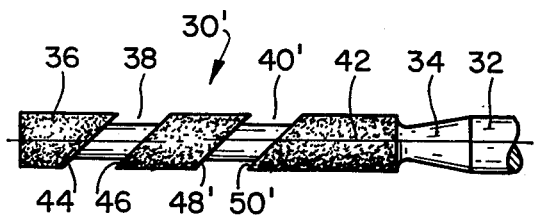
FIG_5
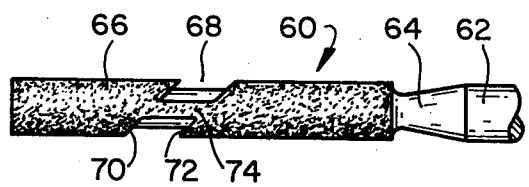
FIG_6
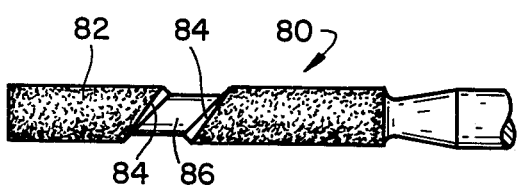
FIG_7
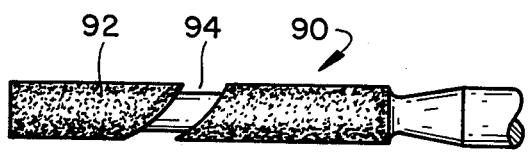
FIG_8

DENTAL BURR

FIELD OF THE INVENTION

This application relates to dental burrs. More specifically, it relates to dental burrs having at least one groove in the cutting surface thereof for providing an oscillatory chip clearing action as the burr rotates.

BACKGROUND OF THE INVENTION

Known, prior art dental burrs include, for example, those shown in U.S. Pat. Nos. 482,558; 2,358,432; 1,813,741; 2,338,437; 2,606,366; 2,901,826; 3,624,095; and 3,894,339; and French Pat. No. 931,489. A further cutting instrument is shown by U.S. Pat. No. 3,510,990.

SUMMARY OF THE INVENTION

The dental burrs of the present invention include a cutting surface having at least one groove therein, each of the grooves in the cutting surface being defined by a plane which encircles the cutting surface at the skewed angle with respect to the axis of rotation of the burr. Each of the grooves can partially or completely encircle the cutting surface, and can be flat, curved or wavey. As shown in the drawings forming a part thereof, one or two (or more) grooves can encircle the cutting surface of the burr. In one embodiment, the angle of the plane of at least one groove in the cutting surface is at an angle with respect to the plane of another groove in the cutting surface (see FIGS. 3 and 4 hereof). In a further embodiment, where there are a plurality, such as two, grooves, the plane of each groove is parallel to the plane(s) of the other groove(s) (see FIG. 5 hereof).

The cutting surface is of conventional configuration, for example, spherical, cylindrical, conical, inverted conical, round, tapered, flame contoured, etc. Uniform configurations, such as spherical or cylindrical, are generally preferred, although other configurations can be utilized if desired. Each planar groove has a pair of side walls which are also skewed with respect to the axis of rotation of the burr. Such side walls, for each groove, can be of any desired configuration, for example, they can be flat and parallel to one another, or they can be beveled and non-parallel, etc.

The grooves function to provide an oscillatory cutting and chip clearing action as the burr rotates, thereby providing fast chip clearance.

BRIEF DESCRIPTION OF THE DRAWINGS

The features and advantages of the present invention will become more apparent from the following detailed description taken together with the accompanying drawings wherein:

FIG. 1 is a perspective view of one embodiment of a dental burr of the present invention;

FIG. 2 is a longitudinal elevational view of the burr of FIG. 1;

FIG. 3 is a perspective view of a further embodiment of the dental burr of the present invention;

FIG. 4 is a longitudinal elevational view of the dental burr of FIG. 3;

FIG. 5 is a longitudinal elevational view of an alternate dental burr of the present invention;

FIG. 6 is a side elevational view of an alternate dental burr of the present invention where the single groove only partially encircles the cutting surface;

FIG. 7 is a side elevational view of a further alternate dental burr of the present invention where the side walls defining the groove are beveled and, therefore, not parallel to each other; and FIG. 8 is a side elevational view of a further alternate dental burr of the present invention where the groove is defined by curved side walls.

Referring to FIGS. 1 and 2, there is shown a dental burr 10 having a shank 12, a neck 14 and a spherical cutting surface 16. A planar groove 18 completely encircles cutting surface 16 at an angle which is skewed to the axis of rotation 20 of burr 10. Groove 18 has flat side walls 22 and 24 which are parallel to one another.

Referring to FIGS. 3 and 4, there is shown a different dental burr 30 having a shank 32, a neck 34 and a cylindrical cutting surface 36. A pair of flat, planar grooves 38 and 40 completely encircle cutting surface 36 at an skewed angle with respect to the axis of rotation 42 of the burr. As shown, the plane of groove 38 is also at an angle with respect to the plane of groove 40. Groove 38 has flat side walls 44 and 46 which are disposed parallel to one another. In a similar manner, groove 40 has flat side walls 48 and 50 which are also disposed parallel to one another.

Referring to FIG. 5, where like numerals have been utilized to indentify like elements of the burr of FIGS. 3 and 4, it is shown that the groove 40', instead of being at an angle with respect to the plane of groove 38, is parallel thereto, thus, flat surfaces 44 and 46 partially defining groove 38 and surfaces 48' and 50' defining groove 40' are all parallel to one another.

In the above embodiments, each of the grooves completely encircles the cutting surface, and the pair of side walls defining each particular grooves are flat and parallel to each other. In the following embodiments, the grooves only partially encircle the cutting surface or the side walls are not flat or parallel to each other.

Referring to FIG. 6, burr 60 has a shank 62, neck 64, and a cutting surface 66. Groove 68 defined, in part, by side walls 70 and 72 only partially encircles the cutting surface, there being a portion 76 of cutting surface 66 at that area where the groove is discontinuous.

Referring to FIG. 7, burr 80 has a cutting surface 82 where the side walls 84 of groove 86 are beveled and therefore not parallel to one another.

Referring to FIG. 8, burr 90 has a cutting surface 92 where the plane of groove 94 is curved.

Although each of the grooves can, in general, be at any angle with respect to the longitudinal axis of the burr, it is desirable that at least one or all of the grooves be at an angle of about 30°–60°, for example 45°, to the longitudinal axis. In this manner, good cutting action and rapid chip clearance is obtained.

The cutting surface of the burrs described herein has abrasive particles (such as diamond, silicon carbide, boron nitride or other particles as known in this art) coated thereon. The abrasive particulate coating is on all or a portion of the cutting surface per se, the side walls of the groove(s) and may or may not be on the bottom wall of the groove(s) since that portion of the burr does not come into contact with the tooth during the grinding or cutting thereof. This coating is shown in the drawings by the textured or speckled appearance of the applicable surfaces.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental burr comprising a shank terminating, at the operative end thereof, in a cutting surface, said cutting surface having a plurality of non-intersecting grooves therein, said non-intersecting grooves being the only grooves in said cutting surface, each of said non-intersecting grooves being defined by a plane which completely encircles said cutting surface at a skewed angle with respect to the axis of rotation of said burr, one of said planes defining one of said non-intersecting grooves being at an angle with respect to the plane defining another of said non-intersecting grooves.

2. The burr of claim 1 wherein each of said non-intersecting grooves has a pair of side walls which are at a skewed angle to the axis of rotation of said burr, said pair of said walls for each non-intersecting groove being flat and parallel to one another.

3. The burr of claim 1 wherein said cutting surface has abrasive particles coated thereon.

4. The burr of claim 1 wherein said cutting surface has two non-intersecting grooves therein.

5. The burr of claim 1 wherein at least one of said non-intersecting grooves has curved side walls.

6. The burr of claim 1 wherein at least one of said non-intersecting grooves has flat side walls.

7. The burr of claim 1 wherein all of said grooves have flat side walls.

* * * * *